s010052080B2

United States Patent
Park

(10) Patent No.: US 10,052,080 B2
(45) Date of Patent: Aug. 21, 2018

(54) MEDICAL IMAGING APPARATUS AND CONTROL METHOD THEREOF

(71) Applicant: SAMSUNG ELECTRONICS CO., LTD., Suwon-si (KR)

(72) Inventor: Min-cheol Park, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 139 days.

(21) Appl. No.: 14/865,817

(22) Filed: Sep. 25, 2015

(65) Prior Publication Data

US 2016/0089105 A1    Mar. 31, 2016

(30) Foreign Application Priority Data

Sep. 26, 2014   (KR) .................. 10-2014-0129524

(51) Int. Cl.
*A61B 6/00*   (2006.01)
*A61B 6/04*   (2006.01)
*A61B 6/02*   (2006.01)

(52) U.S. Cl.
CPC .............. *A61B 6/583* (2013.01); *A61B 6/02* (2013.01); *A61B 6/0414* (2013.01); *A61B 6/488* (2013.01); *A61B 6/542* (2013.01); *A61B 6/502* (2013.01)

(58) Field of Classification Search
CPC ....... A61B 6/0414; A61B 6/488; A61B 6/502; A61B 6/542; A61B 6/583
USPC ............... 378/37, 53, 54, 56, 62, 98.7, 207, 378/108–110
See application file for complete search history.

(56) References Cited

U.S. PATENT DOCUMENTS

| | | | | | |
|---|---|---|---|---|---|
| 5,063,583 A | * | 11/1991 | Galkin | ................ | G03B 42/047 378/165 |
| 5,276,726 A | * | 1/1994 | Galkin | .................... | H05G 1/26 378/173 |
| 5,528,649 A | * | 6/1996 | Heidsieck | ........... | G01N 23/083 378/207 |
| 5,544,238 A | * | 8/1996 | Galkin | .................... | H05G 1/26 378/207 |

(Continued)

FOREIGN PATENT DOCUMENTS

| | | |
|---|---|---|
| DE | 10 2009 017 437 A1 | 10/2010 |
| JP | 2010-204060 A | 9/2010 |
| JP | 2013-47644 A | 3/2013 |

OTHER PUBLICATIONS

International Search Report and Written Opinion, issued by International Searching Authority in corresponding International Application No. PCT/KR2015/010196, dated Jan. 28, 2016 (PCT/ISA/220, PCT/ISA/210 & PCT/ISA/237).

(Continued)

*Primary Examiner* — Allen C. Ho
(74) *Attorney, Agent, or Firm* — Sughrue Mion, PLLC

(57) ABSTRACT

A medical imaging apparatus includes an X-ray radiation unit configured to radiate X-rays onto an object and onto a calibration phantom, which does not overlap the object, according to a first irradiating condition for a pre-shot; a detector configured to detect the X-rays having passed through the object and through the calibration phantom; and a controller configured to acquire calibration information by using a pre-shot image acquired from the detected X-rays, and determine a second irradiating condition for main imaging by using the calibration information.

24 Claims, 12 Drawing Sheets

(56) References Cited

U.S. PATENT DOCUMENTS

| | | | | |
|---|---|---|---|---|
| 5,778,044 A * | 7/1998 | Bruijns | H04N 5/3205 | 348/E3.032 |
| 5,841,835 A * | 11/1998 | Aufrichtig | A61B 6/583 | 378/207 |
| 5,844,965 A * | 12/1998 | Galkin | H05G 1/26 | 378/207 |
| 5,917,877 A * | 6/1999 | Chiabrera | A61B 6/482 | 378/207 |
| 5,964,715 A * | 10/1999 | Thunberg | A61B 90/36 | 378/207 |
| 6,064,716 A * | 5/2000 | Siffert | A61B 6/482 | 378/207 |
| 6,173,038 B1 * | 1/2001 | Siffert | A61B 6/482 | 378/207 |
| 6,377,656 B1 * | 4/2002 | Ueki | A61B 6/4225 | 378/98.7 |
| 6,459,765 B1 * | 10/2002 | Ganin | A61B 6/00 | 378/108 |
| 6,502,984 B2 * | 1/2003 | Ogura | A61B 6/06 | 378/206 |
| 6,570,955 B1 * | 5/2003 | Siffert | A61B 6/482 | 378/207 |
| 6,574,307 B1 * | 6/2003 | Anderton | G06T 5/008 | 378/207 |
| 6,614,877 B2 * | 9/2003 | Anderton | G06T 5/008 | 378/147 |
| 6,632,020 B2 * | 10/2003 | Kaufhold | A61B 6/482 | 378/207 |
| 6,674,835 B2 * | 1/2004 | Kaufhold | A61B 5/4869 | 378/207 |
| 6,683,934 B1 * | 1/2004 | Zhao | A61B 6/032 | 378/37 |
| 6,888,924 B2 * | 5/2005 | Claus | A61B 6/583 | 378/163 |
| 6,990,222 B2 * | 1/2006 | Arnold | A61B 6/583 | 378/18 |
| 7,016,456 B2 * | 3/2006 | Basu | A61B 6/032 | 378/18 |
| 7,116,752 B2 * | 10/2006 | Takahashi | A61B 6/504 | 378/62 |
| 7,173,238 B2 * | 2/2007 | Karasawa | A61B 6/583 | 250/252.1 |
| 7,186,023 B2 * | 3/2007 | Morita | A61B 6/466 | 378/62 |
| 7,238,947 B2 * | 7/2007 | Oumi | G06T 11/005 | 250/370.08 |
| 7,245,694 B2 * | 7/2007 | Jing | A61B 6/025 | 378/37 |
| 7,256,392 B2 * | 8/2007 | Sendai | G06F 19/321 | 250/252.1 |
| 7,387,439 B2 * | 6/2008 | Yang | A61B 6/505 | 378/207 |
| 7,431,500 B2 * | 10/2008 | Deych | A61B 6/482 | 378/111 |
| 7,480,365 B1 * | 1/2009 | Topfer | A61B 6/032 | 378/108 |
| 7,496,176 B2 * | 2/2009 | Aslund | A61B 6/502 | 378/37 |
| 7,545,907 B2 * | 6/2009 | Stewart | A61B 6/02 | 378/108 |
| 7,545,908 B2 * | 6/2009 | Hemmendorff | A61B 6/502 | 378/205 |
| 7,582,860 B2 * | 9/2009 | Kusunoki | A61B 6/583 | 250/252.1 |
| 7,688,940 B2 | 3/2010 | Defreitas et al. | | |
| 7,787,587 B2 * | 8/2010 | Tasaki | A61B 6/4494 | 378/108 |
| 7,866,884 B2 * | 1/2011 | Seto | A61B 6/541 | 378/18 |
| 7,873,198 B2 * | 1/2011 | Shepherd | A61B 6/12 | 382/132 |
| 7,991,106 B2 * | 8/2011 | Ren | A61B 6/025 | 378/21 |
| 8,007,171 B2 * | 8/2011 | Lee | G03B 42/042 | 378/169 |
| 8,126,248 B2 * | 2/2012 | Böhm | A61B 6/583 | 378/4 |
| 8,186,880 B1 * | 5/2012 | Arnold | A61B 6/032 | 378/18 |
| 8,465,204 B2 * | 6/2013 | Kamiya | A61B 10/0275 | 378/204 |
| 8,768,026 B2 * | 7/2014 | Ren | A61B 6/0414 | 382/131 |
| 8,891,849 B2 * | 11/2014 | Rohler | A61B 6/032 | 382/132 |
| 8,938,087 B2 * | 1/2015 | Han | G06T 5/50 | 382/100 |
| 9,014,455 B2 * | 4/2015 | Oh | A61B 6/52 | 378/98.11 |
| 9,097,642 B2 * | 8/2015 | Yin | A61B 6/542 | |
| 9,125,286 B2 * | 9/2015 | De Man | H05G 1/28 | |
| 9,254,113 B2 * | 2/2016 | Kim | A61B 6/4241 | |
| 9,274,037 B2 * | 3/2016 | Huwer | A61B 6/505 | |
| 9,351,700 B2 * | 5/2016 | Li | A61B 6/542 | |
| 9,380,985 B2 * | 7/2016 | Akahori | A61B 6/025 | |
| 9,408,579 B2 * | 8/2016 | Yamakawa | A61B 6/14 | |
| 9,456,796 B2 * | 10/2016 | Han | A61B 6/405 | |
| 9,492,133 B2 * | 11/2016 | Kang | A61B 6/405 | |
| 9,526,471 B2 * | 12/2016 | Goodenough | A61B 6/025 | |
| 9,572,541 B2 * | 2/2017 | Hoshino | A61B 6/5217 | |
| 9,603,577 B2 * | 3/2017 | Oh | A61B 6/484 | |
| 9,681,851 B2 * | 6/2017 | Rohler | A61B 6/583 | |
| 9,730,669 B2 * | 8/2017 | Lee | A61B 6/545 | |
| 9,805,449 B2 * | 10/2017 | Morita | A61B 6/502 | |
| 9,814,435 B2 * | 11/2017 | Kim | A61B 6/469 | |
| 2003/0095695 A1 | 5/2003 | Arnold | | |
| 2004/0252811 A1 | 12/2004 | Morita et al. | | |
| 2004/0264648 A1 | 12/2004 | Claus et al. | | |
| 2005/0192495 A1 | 9/2005 | Makram-Ebeid et al. | | |
| 2009/0268865 A1 | 10/2009 | Ren et al. | | |
| 2011/0168878 A1 | 7/2011 | Hoerndler et al. | | |

OTHER PUBLICATIONS

Communication dated Sep. 13, 2017 by the European Patent Office in counterpart European Patent Application No. 15844117.0.

* cited by examiner

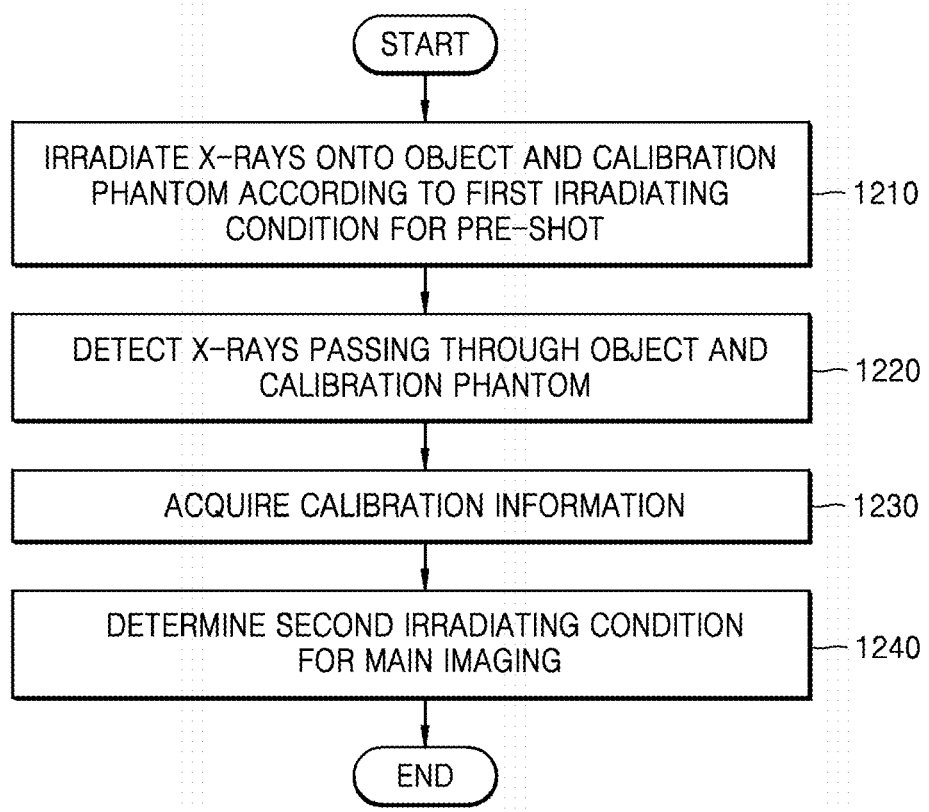

MEDICAL IMAGING APPARATUS AND CONTROL METHOD THEREOF

CROSS-REFERENCE TO RELATED APPLICATION

This application claims priority from Korean Patent Application No. 10-2014-0129524, filed on Sep. 26, 2014, in the Korean Intellectual Property Office, the disclosure of which is incorporated herein in its entirety by reference.

BACKGROUND

1. Field

Apparatuses and methods consistent with exemplary embodiments relate to a medical imaging apparatus and a control method thereof, and more particularly, to a medical imaging apparatus and a control method thereof, which image an object along with a calibration phantom, to perform calibration during imaging operation.

2. Description of the Related Art

Medical image processing apparatuses acquire an internal structure of an object as an image. Medical image processing apparatuses are noninvasive examination apparatuses that show the structural details, internal tissue, and fluid flow of a human body. A user such as a doctor diagnoses a health state and a disease of a patient by using a medical image output from a medical image processing apparatus. Examples of apparatuses for capturing and generating a medical image include magnetic resonance imaging (MRI) apparatuses, computed tomography (CT) apparatuses, X-ray apparatuses, and ultrasound apparatuses.

The X-ray apparatuses irradiate X-rays onto an object and acquire an image of the object by using the X-rays having passed through the object. Since a transmissivity of an X-ray varies depending on a characteristic of a material forming an object, an internal structure of the object may be imaged by detecting intensity or strength of the X-ray having passed through the object.

The related art X-ray apparatuses include an auto exposure control (AEC) calibration feature for optimizing an X-ray irradiating condition for imaging an object.

However, in the related art, the AEC calibration is performed when a component of the X-ray apparatus, such as a high voltage generator (HVG) which changes a beam quality of an X-ray, an X-ray tube, or the like, is changed, and/or periodically, for example, once in two to three months.

Generally, the main components of the X-ray apparatus such as an HVG, an X-ray tube, a detector, etc., cause an error during an imaging operation. For this reason, in a related art, the system information at a time when the calibration is performed differs from the system information at a time of actual imaging, and, thus, a performance of the X-ray apparatus may become less effective.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments include a medical imaging apparatus and a control method thereof, which perform calibration in each imaging.

According to an aspect of an exemplary embodiment, a medical imaging apparatus includes: an X-ray radiation unit that irradiates an X-ray onto an object and a calibration phantom, which does not overlap the object, according to a first irradiating condition for pre-shot; a detector that detects the X-ray passing through the object and the calibration phantom; and a controller that acquires calibration information by using a pre-shot image acquired from the detected X-ray, and determines a second irradiating condition for main imaging by using the calibration information.

The controller may acquire a density of the object, based on a pixel value of the calibration phantom included in the pre-shot image.

The controller may determine the second irradiating condition, based on the density of the object acquired based on the pre-shot image.

The calibration phantom may include a first calibration phantom having a single thickness and a single density, and the controller may perform offset correction on pre-stored calibration information by using the pre-shot image acquired from the detected X-ray passing through the first calibration phantom.

The pre-stored calibration information may be acquired by imaging a plurality of second calibration phantoms before pre-shot.

The calibration phantom may include a plurality of third calibration phantoms in which at least one selected from thicknesses and densities differ, and the controller may acquire a pre-shot image from an X-ray detected for each of the plurality of third calibration phantoms, and acquire calibration information by using the acquired pre-shot image.

The controller may acquire, from the pre-shot image, a pixel value of the object and a pixel value for each of the plurality of third calibration phantoms, acquire a first relational equation between a thickness and a pixel value from the plurality of third calibration phantoms having different thicknesses for each of a plurality of different densities by using the acquired pixel value, acquire a second relational equation between a density and a pixel value for a thickness of the object by using a plurality of the first relational equations acquired for the plurality of different densities, acquire a density of the object by using the second relational equation and a pixel value of the object, and determine the second irradiating condition for main imaging by using the acquired density of the object.

The controller may acquire a pixel value of the object and a pixel value for each of the plurality of third calibration phantoms from the pre-shot image, calculate a density of the object from Equation (1), which is the second relational equation for a thickness of the object, by using the acquired pixel value, and determine the second irradiating condition for main imaging by using the calculated density of the object:

$$\text{ob\_den} = a \times \text{ob\_PV} + b \tag{1}$$

where ob_den denotes a density of the object, ob_PV denotes a pixel value of the object, and a and b denote coefficients which are calculated by using a pixel value and a density for each of the plurality of third calibration phantoms.

The calibration phantom may be disposed not to overlap the object on the detector.

The calibration phantom may be disposed between the X-ray radiation unit and the detector not to overlap the object.

The calibration phantom may have a stair shape to acquire data for different thicknesses.

The medical imaging apparatus may further include an output unit that displays an image of the object which is imaged according to the second irradiating condition.

The output unit may display a usage state of the calibration phantom, and the usage state may include at least one selected from whether to use the calibration phantom and a position of the calibration phantom in the detector.

The controller may control a support, which supports the calibration phantom, to adjust a position of the calibration phantom.

According to an aspect of an exemplary embodiment, a control method performed by a medical imaging apparatus includes: irradiating an X-ray onto an object and a calibration phantom, which does not overlap the object, according to a first irradiating condition for pre-shot; detecting the X-ray passing through the object and the calibration phantom; acquiring calibration information by using a pre-shot image acquired from the detected X-ray; and determining a second irradiating condition for main imaging by using the calibration information.

The acquiring of the calibration information may include acquiring a density of the object, based on a pixel value of the calibration phantom included in the pre-shot image, and the determining of the second irradiating condition may include determining the second irradiating condition, based on the density of the object.

The calibration phantom may include a first calibration phantom having a single thickness and a single density, and the acquiring of the calibration information may include performing offset correction on pre-stored calibration information by using the pre-shot image acquired from the detected X-ray passing through the first calibration phantom.

The pre-stored calibration information may be acquired by imaging a plurality of second calibration phantoms before pre-shot.

The calibration phantom may include a plurality of third calibration phantoms in which at least one selected from thicknesses and densities differ, and the acquiring of the calibration information may include: acquiring a pre-shot image from an X-ray detected for each of the plurality of third calibration phantoms; and acquiring calibration information by using the acquired pre-shot image.

The acquiring of the calibration information may include: acquiring, from the pre-shot image, a pixel value of the object and a pixel value for each of the plurality of third calibration phantoms; acquiring a first relational equation between a thickness and a pixel value from the plurality of third calibration phantoms having different thicknesses for each of a plurality of different densities by using the acquired pixel value; acquiring a second relational equation between a density and a pixel value for a thickness of the object by using a plurality of the first relational equations acquired for the plurality of different densities; and acquiring a density of the object by using the second relational equation and a pixel value of the object. The determining of the second irradiating condition may include determining the second irradiating condition for main imaging by using the acquired density of the object.

The acquiring of the calibration information may include: acquiring a pixel value of the object and a pixel value for each of the plurality of third calibration phantoms from the pre-shot image; and calculating a density of the object from Equation (1), which is the second relational equation for a thickness of the object, by using the acquired pixel value $$\text{ob\_den} = a \times \text{ob\_PV} + b \quad (1)$$

where ob_den denotes a density of the object, ob_PV denotes a pixel value of the object, and a and b denote coefficients which are calculated by using a pixel value and a density for each of the plurality of third calibration phantoms.

The determining of the second irradiating condition may include determining the second irradiating condition for main imaging by using the calculated density of the object.

The control method may further include displaying an image of the object which is imaged according to the second irradiating condition.

According to an aspect of an exemplary embodiment, a medical imaging apparatus includes: a X-ray irradiation unit that generates an X-ray to irradiate the X-ray onto an object; a compression unit that compresses the object and an image acquisition unit that receives the X-ray irradiated onto the object and acquires X-ray image information of the object, wherein the image acquisition unit includes one or more calibration phantoms, when irradiating the X-ray, the image acquisition unit acquires calibration phantom image information and the X-ray image information of the object.

An irradiating condition to a density is corrected from the calibration phantom image.

The X-ray irradiation unit irradiates the X-ray onto the object, based on the irradiating condition.

The image acquisition unit includes a detector or a bucky, and the calibration phantom is coupled to one selected from the detector and the bucky.

According to an aspect of an exemplary embodiment, a method of controlling a medical imaging apparatus, the method includes: irradiating a first amount of X-rays onto an object; acquiring X-ray image information of the object and X-ray image information of a calibration phantom; correcting an irradiating condition from a phantom image; and irradiating a second amount of X-rays corresponding to a density of the object, based on a result of the correction.

The correcting of the irradiating condition includes correcting an X-ray irradiation amount condition to a density of the calibration phantom.

The irradiating includes determining a density of the object when irradiating the first amount of X-rays.

BRIEF DESCRIPTION OF THE DRAWINGS

The above and/or other aspects will become apparent by describing certain exemplary embodiments, with reference to the accompanying drawings, in which:

FIG. 12 is a flowchart illustrating a control method of a medical imaging apparatus according to an exemplary embodiment.

DETAILED DESCRIPTION

Figure 1:
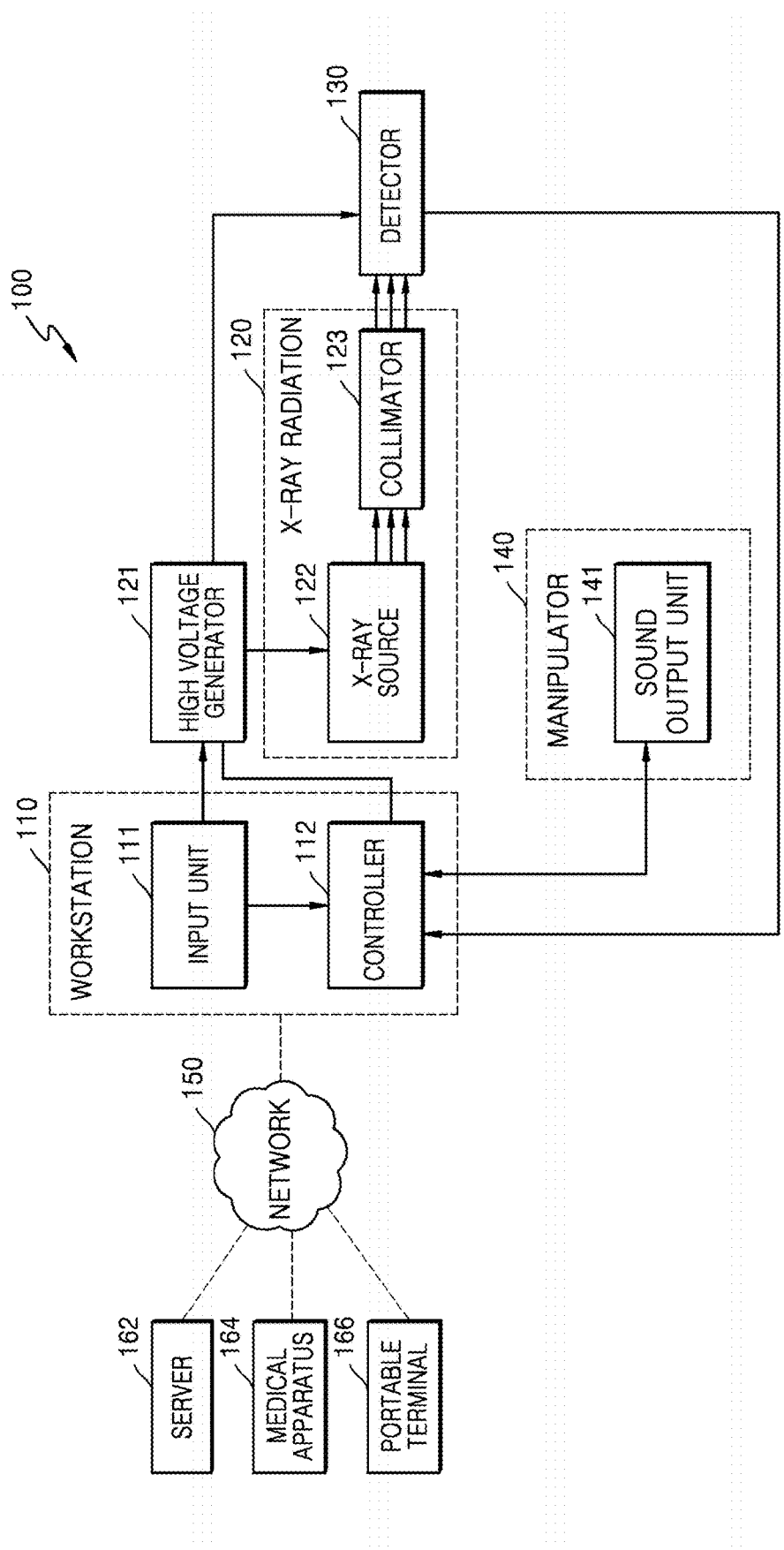
FIG. 1 is a diagram illustrating a configuration of an X-ray apparatus.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Throughout the specification, it will be understood that when a component "includes" an element, unless there is another opposite description thereto, it should be understood that the component does not exclude another element and may further include another element. Also, the term "unit" in the exemplary embodiments means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Throughout the specification, an "image" may mean multi-dimensional data formed of discrete image elements, e.g., pixels in a two-dimensional (2D) image and voxels in a three-dimensional (3D) image. For example, an image may include medical images of an object acquired by an X-ray, a CT, an MRI, an ultrasound wave, and other medical image systems.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof.

A phantom used herein is a model which is used instead of a human body, for determining an amount of radiation applied to a human body and denotes an object which is used for measuring attenuation and scattering of radiation or a distribution of radioactive materials in the object. The phantom may include a spherical phantom which has characteristic close to a density of organisms and an effective atomic number and has a temper similar to a human body. Examples of a shape of the phantom may include a spherical shape, a hexahedron, and a stair shape, but are not limited thereto.

Furthermore, throughout the specification, a "user" may be, but is not limited to, a medical expert, such as a medical doctor, a nurse, a medical laboratory technologist, a medical image expert, or a technician who repairs a medical apparatus.

Examples of a medical imaging apparatus used may include a CT apparatus and an X-ray apparatus which transmit X-rays through a human body to acquire an image of an internal structure of the human body. In the present specification, the X-ray apparatus will be described as an example.

An X-ray apparatus is a medical imaging apparatus that acquires images of internal structures of an object by transmitting an X-ray through the human body. The X-ray apparatus may acquire medical images of an object more simply within a shorter time than other medical imaging apparatuses including an MRI apparatus and a CT apparatus. Therefore, the X-ray apparatus is widely used in a chest imaging, abdomen imaging, skeleton imaging, nasal sinuses imaging, neck soft tissue imaging, and breast imaging. The X-ray apparatus may include a controller, and may adjust a parameter for radiating an X-ray, for optimizing an X-ray irradiating condition. For example, the controller may analyze a pre-shot image and set a parameter optimized for a characteristic of an object.

FIG. 1 is a block diagram of an X-ray apparatus 100.

The X-ray apparatus 100 shown in FIG. 1 may be a fixed-type X-ray apparatus or a mobile X-ray apparatus.

Referring to FIG. 1, the X-ray apparatus 100 includes a workstation 110, an X-ray radiation unit 120, a high voltage generator 121, and a detector 130.

The workstation 110 includes an input unit 111 through which a user may input commands for manipulating the X-ray apparatus 100 including an X-ray irradiation, and a controller 112 controlling operations of the X-ray apparatus 100.

The high voltage generator 121 generates a high voltage for generating X-rays, and applies the high voltage to an X-ray source 122.

The X-ray radiation unit 120 includes the X-ray source 122 receiving the high voltage applied from the high voltage generator 121 to generate and irradiate the X-ray, and a collimator 123 for guiding a path of the X-ray irradiated from the X-ray source 122.

The detector 130 detects an X-ray that is radiated from the X-ray radiator 120 and has been transmitted through an object. The detector 130 may be implemented in, for example, a table type or a stand type. A material of a detector may include amorphous silicon (a-Si) or HgI.

The X-ray apparatus 100 may further include a manipulation unit 140 including a sound output unit 141 outputting sound representing information relating to imaging operation such as the X-ray irradiation under a control of the controller 112. For example, the controller 112 may determine a parameter, as for example, at least one of a tube voltage, a tube current, a target material, a positive target material, an exposure time, threshold energy, a filter, etc., and may set an irradiating condition, based on the parameter, for performing imaging of the object.

The workstation 110, the X-ray radiation unit 120, the high voltage generator 121, and the detector 130 may be connected to each other via wires or wirelessly. If they are connected to each other wirelessly, a device (not shown) for synchronizing clocks with each other may be further included.

The input unit 111 may include a keyboard, a mouse, a touch screen, a voice recognizer, a fingerprint recognizer, an iris recognizer, and the like. The user may input a command for irradiating the X-ray via the input unit 111, and to do this, the input unit 111 may include a switch for inputting the command. The switch may be configured so that an irradiation command for irradiating the X-ray may be input only when the switch is pushed twice.

That is, when the user pushes the switch, a prepare command for performing a pre-heating operation for X-ray irradiation may be input through the switch, and then, when the user pushes the switch once more, the irradiation command for irradiating the X-ray may be substantially input through the switch. When the user manipulates the switch as described above, the input unit 111 generates signals corresponding to the commands input through the switch manipulation, that is, a prepare signal and an irradiation signal, and outputs the generated signals to the high voltage generator 121 generating a high voltage for generating the X-ray.

When the high voltage generator 121 receives the prepare signal output from the input unit 111, the high voltage generator 121 starts a pre-heating operation, and when the pre-heating is finished, the high voltage generator 121 outputs a ready signal to the controller 112. The detector 130 also needs to prepare for detecting the X-ray, and thus, when the high voltage generator 121 receives the prepare signal output from the input unit 111, the high voltage generator 121 outputs a prepare signal to the detector 130 at the same time of performing the pre-heating operation, so that the detector 130 may prepare for detecting the X-ray transmitted through the object. The detector 130 prepares for detecting the X-ray when receiving the prepare signal, and when the preparing for the detection is finished, the detector 130 outputs a ready signal to the high voltage generator 121 and the controller 112.

When the pre-heating operation of the high voltage generator 121 is finished, the detector 130 is ready for the detecting the X-ray, and the irradiation signal is output from the input unit 111 to the high voltage generator 121, the high voltage generator 121 generates and applies the high voltage to the X-ray source 122, and the X-ray source 122 irradiates the X-ray.

When the irradiation signal is output from the input unit 111, the controller 112 may output a sound output signal to the sound output unit 141 so that the sound output unit 141 outputs predetermined sound and the object may recognize the irradiation of X-ray. The sound output unit 141 may output sound representing other information relating to the imaging, in addition to the X-ray irradiation. In FIG. 1, the sound output unit 141 is included in the manipulation unit 140; however, the exemplary embodiments are not limited thereto, and the sound output unit 141 may be located at a different location from the manipulation unit 140. For example, the sound output unit 141 may be included in the workstation 110, or may be located on a wall surface of an examination room in which the X-ray imaging of the object is performed.

The controller 112 controls locations of the X-ray radiation unit 120 and the detector 130, a imaging timing, and imaging conditions according to imaging conditions set by the user.

In more detail, the controller 112 controls the high voltage generator 121 and the detector 130 according to the command input via the input unit 111 so as to control an irradiation timing of the X-ray, an intensity of the X-ray, and an irradiation region of the X-ray. The controller 112 adjusts the location of the detector 130 according to a predetermined imaging condition, and controls an operation timing of the detector 130.

The controller 112 generates a medical image of the object by using image data transmitted from the detector 130. In detail, the controller 112 receives the image data from the detector 130, and then, generates the medical image of the object by removing noise in the image data, and adjusting a dynamic range and interleaving of the image data.

The X-ray apparatus 100 shown in FIG. 1 may further include an output unit (not shown) for outputting the medical image generated by the controller 112. The output unit may output information that is necessary for the user to manipulate the X-ray apparatus 100, for example, a user interface (UI), user information, or object information. The output unit may include a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a primary flight display (PFD), a three-dimensional (3D) display, a transparent display, and other various output devices well known in the art.

The workstation 110 shown in FIG. 1 may further include a communication unit (not shown) that may be connected to a server 162, a medical apparatus 164, and a portable terminal 166 via a network 150.

The communication unit may be connected to the network 150 via wires or wirelessly to communicate with the external server 162, the external medical apparatus 164, or the external portable terminal 166. The communication unit may transmit or receive data relating to diagnosis of the object via the network 150, and may transmit or receive medical images captured by the other medical apparatus 164, for example, a CT, an MRI, or an X-ray apparatus. Moreover, the communication unit may receive medical history or treatment schedule of an object, e.g., a patient, from the server 162 to diagnose a disease of the object. The communication unit may perform data communication with the portable terminal 166 such as a mobile phone of a doctor or a patient, a personal digital assistant (PDA), or a laptop computer, as well as the server 162 or the medical apparatus 164 in a hospital.

The communication unit may include one or more elements enabling to communicate with external apparatuses, for example, a short distance communication module, a wired communication module, and a wireless communication module.

The short distance communication module is a module for communicating with a device located within a predetermined distance. The short distance communication technology may be wireless local area network (LAN), Wi-Fi, Bluetooth, Zigbee, Wi-Fi Direct (WFD), ultra wideband (UWD), infrared data association (IrDA), Bluetooth low energy (BLE), near field communication (NFC), or the like; however, the exemplary embodiments are not limited thereto.

The wired communication module is a module for communicating by using an electric signal or an optical signal, and the wired communication technology may be wired communication technology using a pair cable, a coaxial cable, or an optical fiber cable, and a wired communication technology that is well known in the art.

The wireless communication module may transmit/receive a wireless signal to/from at least one of a base, an external device, and a server in a mobile communication network. Here, the wireless signal may be a voice call signal, a video call signal, or various types of data according to text/multimedia messages transmission.

The X-ray apparatus 100 shown in FIG. 1 may include a plurality of digital signal processors (DSPs), an ultra-small calculator, and a processing circuit for specialized usage (for example, a high speed analog/digital (A/D) conversion, a high speed Fourier transformation, an array process, etc.

The communication between the workstation 110 and the X-ray radiation unit 120, the workstation 110 and the high voltage generator 121, and the workstation 110 and the detector 130 may use a high speed digital interface, such as low voltage differential signaling (LVDS), asynchronous serial communication, such as universal asynchronous receiver transmitter (UART), synchronous serial communication, or a low latency network protocol, such as a controller area network (CAN), and other various communication methods that are well known in the art may be used.

Figure 2:
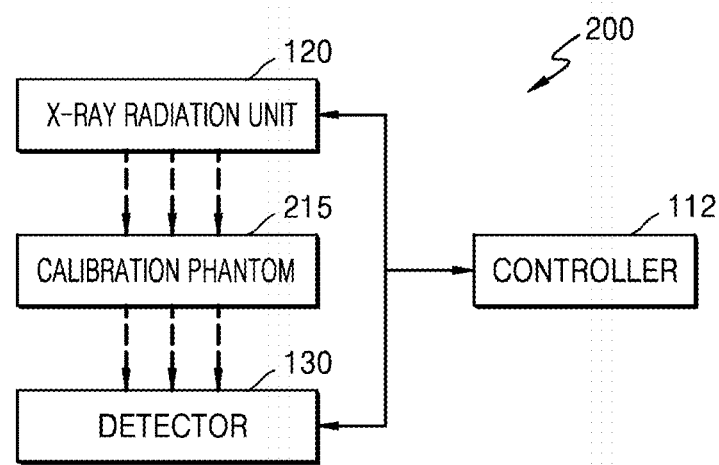
FIG. 2 is a block diagram illustrating a medical imaging apparatus according to an exemplary embodiment.

FIG. 2 is a block diagram illustrating a medical imaging apparatus 200 according to an exemplary embodiment.

As illustrated in FIG. 2, the medical imaging apparatus 200 according to an exemplary embodiment may include an X-ray radiation unit 120, a detector 130, a controller 112, and one or more calibration phantoms 215. The medical imaging apparatus 200 may include additional elements, in addition to the illustrated elements. Alternatively, the medical imaging apparatus 200 may include fewer elements than the number of illustrated elements. The medical imaging apparatus 200 may be a breast imaging apparatus.

The X-ray radiation unit 120 irradiates X-rays onto an object and the calibration phantom 215, which is disposed not to overlap the object, according to a first irradiating condition for a pre-shot. The detector 130 detects the X-rays having passed through the object and the calibration phantom 215. The controller 112 acquires calibration information by using a pre-shot image acquired from the detected X-rays, and determines a second irradiating condition for main imaging by using the calibration information.

In detail, the controller 112 according to an exemplary embodiment may acquire a density of an object, based on a pixel value of the calibration phantom 215 included in the pre-shot image. The controller 112 may determine the second irradiating condition, based on a density of the object acquired based on the pre-shot image.

According to an exemplary embodiment, the calibration phantom 215 may have a single thickness and a single density. In this case, the controller 112 may perform offset correction on pre-stored calibration information by using the pre-shot image acquired from the detected X-rays having passed through the calibration phantom 215. The pre-stored calibration information may be acquired by imaging a plurality of calibration phantoms, which differ from the calibration phantom 215, before pre-shot. The controller 112 may determine the second irradiating condition for main imaging by using the calibration information for which the offset correction has been performed. This will be described below in detail with reference to FIG. 5.

According to an exemplary embodiment, at least one of the calibration phantoms 215 may have a thickness and/or a density different from other phantoms. The controller 112 may acquire a pre-shot image from X-rays detected for the plurality of calibration phantoms in which at least one selected from thicknesses and densities differ, and acquire calibration information by using the acquired pre-shot image. The controller 112 may determine the second irradiating condition for main imaging by using the acquired calibration information. This will be described below in detail with reference to FIG. 7.

According to an exemplary embodiment, the calibration phantom 215 having a small size may be provided to perform calibration when imaging the actual object. Accordingly, a time difference existing in a related art between a calibration timing and an imaging timing of an actual object may be eliminated and, thus, a more accurate calibration is performed and whether to perform calibration may be selected by using a movable phantom structure in imaging.

Figure 3:
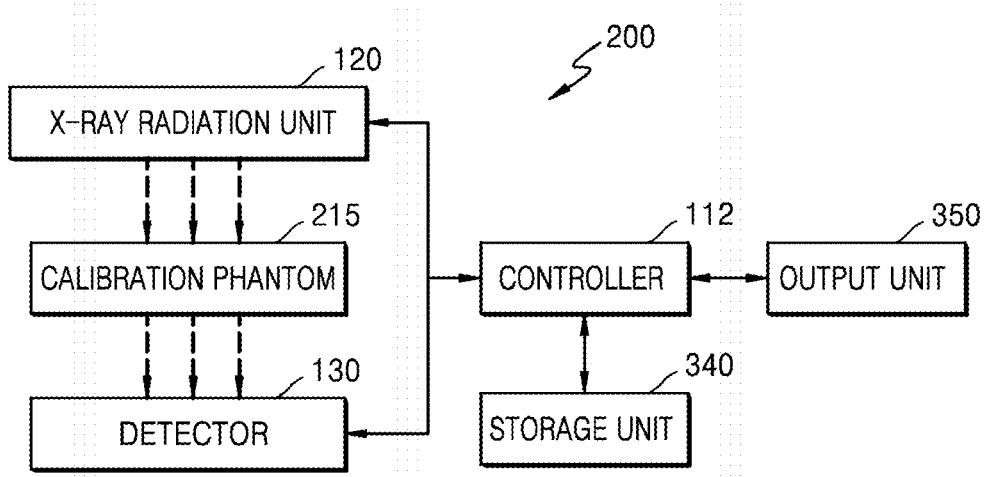
FIG. 3 is a block diagram illustrating additional elements of a medical imaging apparatus according to an exemplary embodiment.

FIG. 3 is a block diagram illustrating additional elements of the medical imaging apparatus 200 according to an exemplary embodiment.

As illustrated in FIG. 3, the medical imaging apparatus 200 according to an exemplary embodiment may include the X-ray radiation unit 120, the detector 130, the controller 112, the calibration phantom 215, a storage unit 340, and an output unit 350. The medical imaging apparatus 200 may include additional elements, in addition to the illustrated elements. Alternatively, the medical imaging apparatus 200 may include fewer elements than the number of illustrated elements.

The X-ray radiation unit 120, the detector 130, the controller 112, and the calibration phantom 215 illustrated in FIG. 3 respectively correspond to the X-ray radiation unit 120, the detector 130, the controller 112, and the calibration phantom 215 illustrated in FIG. 2, and thus, the same descriptions provided with regard to FIG. 2 are not repeated.

The storage unit 340 may store calibration information.

The storage unit 340 according to an exemplary embodiment may store the calibration information which is acquired by imaging a plurality of calibration phantoms before pre-shot. The medical imaging apparatus 200 may perform offset correction on the calibration information stored in the storage unit 340 by using a pre-shot image acquired from the detected X-rays having passed through the calibration phantom 215.

The output unit 350 may display an image of an imaged object.

The output unit 350 according to an exemplary embodiment may display the image of the object which is imaged according to a second irradiating condition, which is determined by using the calibration information, for main imaging.

The output unit 350 according to an exemplary embodiment may display a usage state of the calibration phantom 215. For example, the usage state may include at least one selected from whether to use the calibration phantom 215, a position of the calibration phantom 215 in the detector 130, the number of used calibration phantoms 215, and a type of a used calibration phantom 215. This will be described below in detail with reference to FIGS. 10 and 11.

Figure 4C:
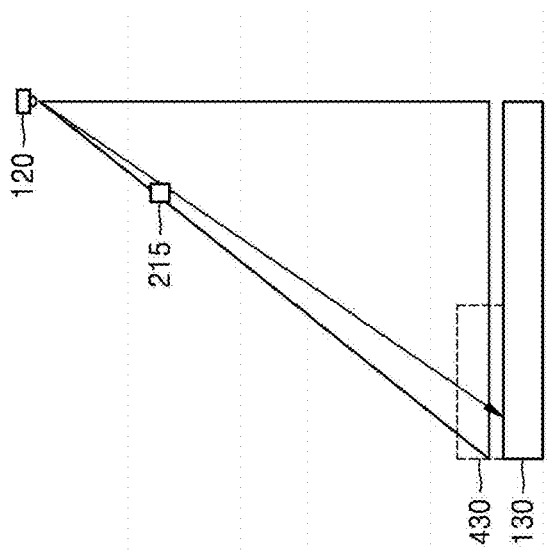
FIGS. 4A, 4B, and 4C are exemplary diagrams illustrating a position of a calibration phantom according to an exemplary embodiment.
Figure 4B:
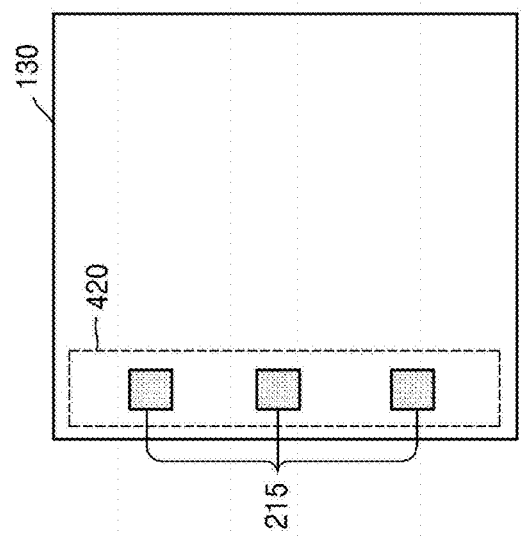
Figure 4A:
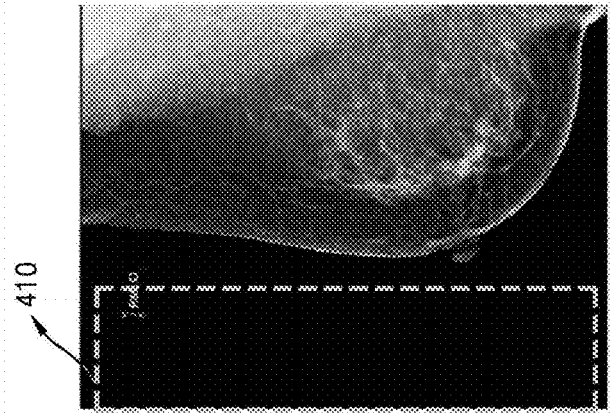

FIGS. 4A, 4B, and 4C are exemplary diagrams illustrating a position of a calibration phantom according to an exemplary embodiment.

The calibration phantom 215 according to an exemplary embodiment is disposed not to overlap an object on the detector 130.

According to an exemplary embodiment, the calibration phantom 215 may be disposed between the X-ray radiation unit 120 and the detector 130 not to overlap an object.

For example, referring to FIG. 4A, when the medical imaging apparatus 200 is a mammography apparatus, an object is not located in a region 410 opposite to a chest wall on the detector 130. Therefore, in the mammography apparatus, the region 410 on the detector 130 which corresponds to the chest wall is a region in which the calibration phantom 215 may be disposed to not overlap the object, i.e., the breast.

FIG. 4B is an exemplary diagram illustrating that the calibration phantom 215 is disposed in the detector 130 according to an exemplary embodiment.

The calibration phantom 215 may be disposed in a region 420 which does not overlap an object on the detector 130, and may be imaged along with the object.

For example, the calibration phantom 215 may be adhered and fixed to the region 420 which does not overlap the object on the detector 130.

As another example, a position of the calibration phantom 215 may be changed each time an object is imaged. Also, when the region 420 which does not overlap the object is changed during imaging, the position of the calibration phantom 215 may be adjusted not to overlap the object.

FIG. 4C is an exemplary diagram illustrating that the calibration phantom 215 is disposed in a space between the detector 130 and the X-ray radiation unit 120 according to an exemplary embodiment.

The calibration phantom 215 may be disposed in the space between the detector 130 and the X-ray radiation unit 120 so as to be detected in a region 430 which does not overlap an object on the detector 130.

For example, the calibration phantom 215 may be fixed by a separate support (not shown) connected to the medical imaging apparatus 200. Also, a position of the calibration phantom 215 may be adjusted by the separate support (not shown) connected to the medical imaging apparatus 200. When the region 430 which does not overlap the object is changed during imaging, the position of the calibration phantom 215 may be adjusted not to overlap the object.

Figure 5:
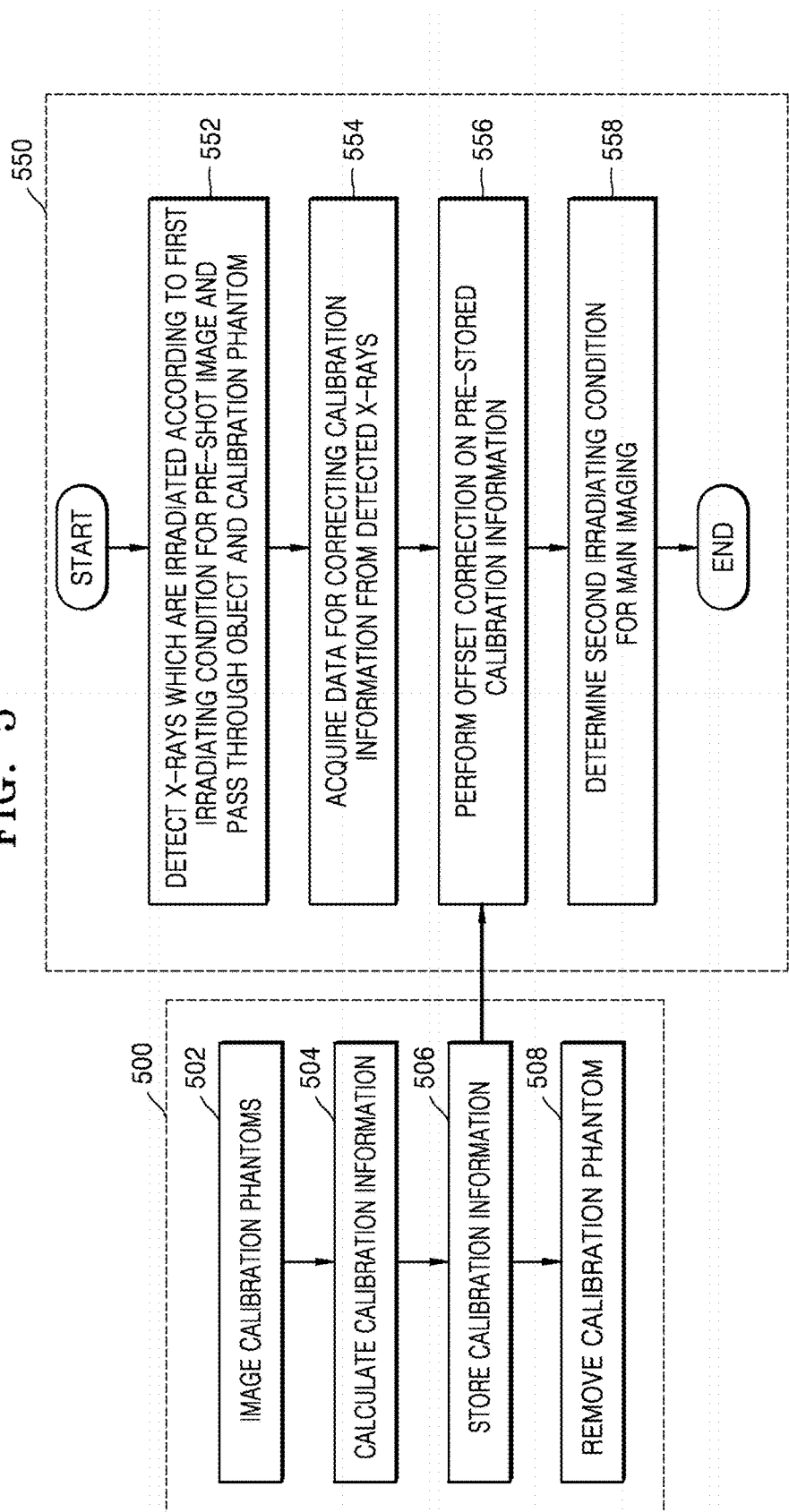
FIG. 5 is a flowchart illustrating a method of performing calibration by using a calibration phantom having a single thickness and a single density, according to an exemplary embodiment.

FIG. 5 is a flowchart illustrating a method of performing calibration by using a calibration phantom having a single thickness and a single density, according to an exemplary embodiment.

A process of performing calibration by using the continuously provided calibration phantom 215 having a single thickness and a single density according to an exemplary embodiment may include a pre-calibration process 500, which is performed before imaging an object, and a real-time calibration process 550 which is performed when imaging the object.

In operation 502 of the pre-calibration process 500, the medical imaging apparatus 200 according to an exemplary embodiment may image a plurality of calibration phantoms which includes at least one calibration phantom having a density and/or a thickness different from other calibration phantoms. The medical imaging apparatus 200 may detect X-rays having passed through the calibration phantoms.

In operation 504, the medical imaging apparatus 200 according to an exemplary embodiment may acquire calibration information by using an image acquired from the detected X-rays.

In operation 506, the medical imaging apparatus 200 according to an exemplary embodiment may store the calibration information. The stored calibration information is used for offset correction in operation 556 to be described below.

In operation 508, the calibration phantom may be removed by the medical imaging apparatus 200 at the end of the pre-calibration process 500.

The real-time calibration process 550 is performed when imaging the object and consequently to performing the pre-calibration process 500. In operation 552, the medical imaging apparatus 200 according to an exemplary embodiment may detect X-rays which are irradiated according to a first irradiating condition for pre-shot and pass through the object and the calibration phantom 215. In detail, the medical imaging apparatus 200 may irradiate the X-rays onto the object and the calibration phantom 215, which is disposed not to overlap the object, according to the first irradiating condition for pre-shot and detect the X-rays having passed through the object and the calibration phantom 215.

In operation 554, the medical imaging apparatus 200 according to an exemplary embodiment may acquire data for correcting calibration information from a pre-shot image acquired from the detected X-rays having passed through the calibration phantom 215.

In operation 556, the medical imaging apparatus 200 according to an exemplary embodiment may perform offset correction on pre-stored calibration information. The pre-stored calibration information is the information that is acquired from an image, which is captured for calibration separately from imaging of an object, and stored. For example, the pre-stored calibration information may include the calibration information acquired in the pre-calibration process 500.

In operation 558, the medical imaging apparatus 200 according to an exemplary embodiment may determine a second irradiating condition for main imaging.

Figure 6B:
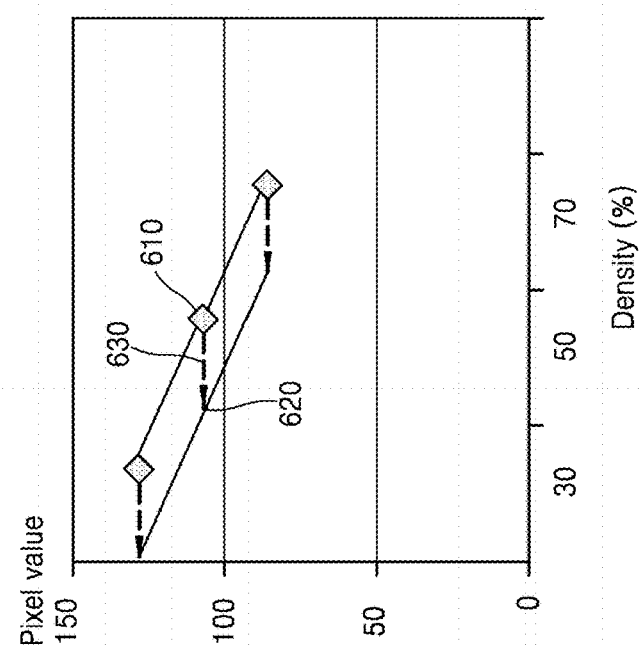
FIGS. 6A and 6B are exemplary diagrams for describing offset correction for pre-stored calibration information according to the method of FIG. 5.
Figure 6A:
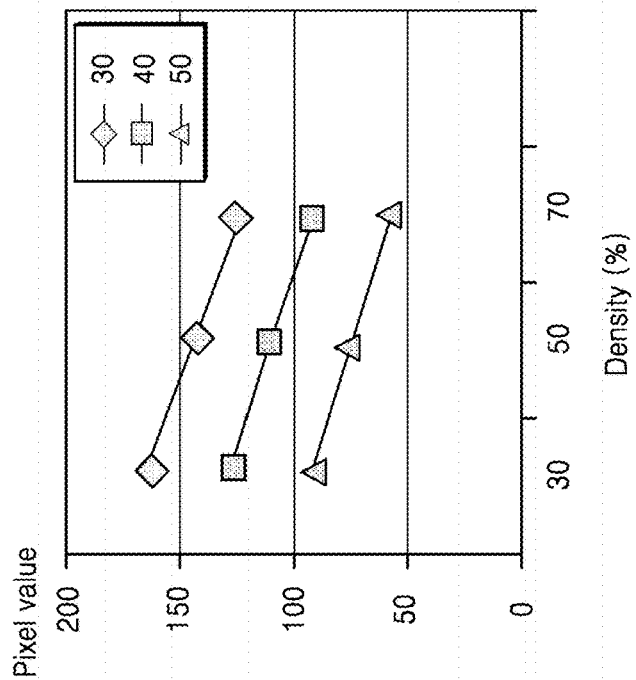

FIGS. 6A and 6B are exemplary diagrams for describing offset correction for pre-stored calibration information according to the method of FIG. 5.

FIG. 6A is a graph showing a pixel value for a density of the calibration phantom which is acquired in the pre-calibration process 500 which is performed before imaging the object.

For example, referring to FIG. 6A, the medical imaging apparatus 200 may acquire an image by imaging a plurality of calibration phantoms which have a density of 30% and respectively have thicknesses of 30 mm, 40 mm, and 50 mm, a plurality of calibration phantoms which have a density of 50% and respectively have thicknesses of 30 mm, 40 mm, and 50 mm, and a plurality of calibration phantoms which have a density of 70% and respectively have thicknesses of 30 mm, 40 mm, and 50 mm, and may acquire a pixel value for each of the calibration phantoms by using the image. The medical imaging apparatus 200 may store information about a relationship between a density of a calibration phantom having a certain thickness and a pixel value.

FIG. 6B is a graph showing that offset correction is performed for pre-stored calibration information by using the continuously provided calibration phantom 215 having a single thickness and a single density.

For example, it is assumed that a calibration phantom 215 having a thickness of 40 mm and a density of 50% is used for real-time calibration. Referring to FIG. 6B, a pixel value 620 which is acquired by imaging an object and the calibration phantom 215 having a thickness of 40 mm and a density of 50% is less than a pixel value 610 of the calibration phantom 215, having a thickness of 40 mm and a density of 50%, which is pre-stored as calibration information. In this case, as shown in FIG. 6B, the medical imaging apparatus 200 may adjust the pre-stored calibration information by a difference 630 (as illustrated by an arrow) between the pre-stored pixel value 610 and the pixel value 620 which is acquired when imaging the object. That is, the medical imaging apparatus 200 may perform offset correction on information about a relationship between a density of a calibration phantom having a certain thickness and a pixel value.

Figure 7:
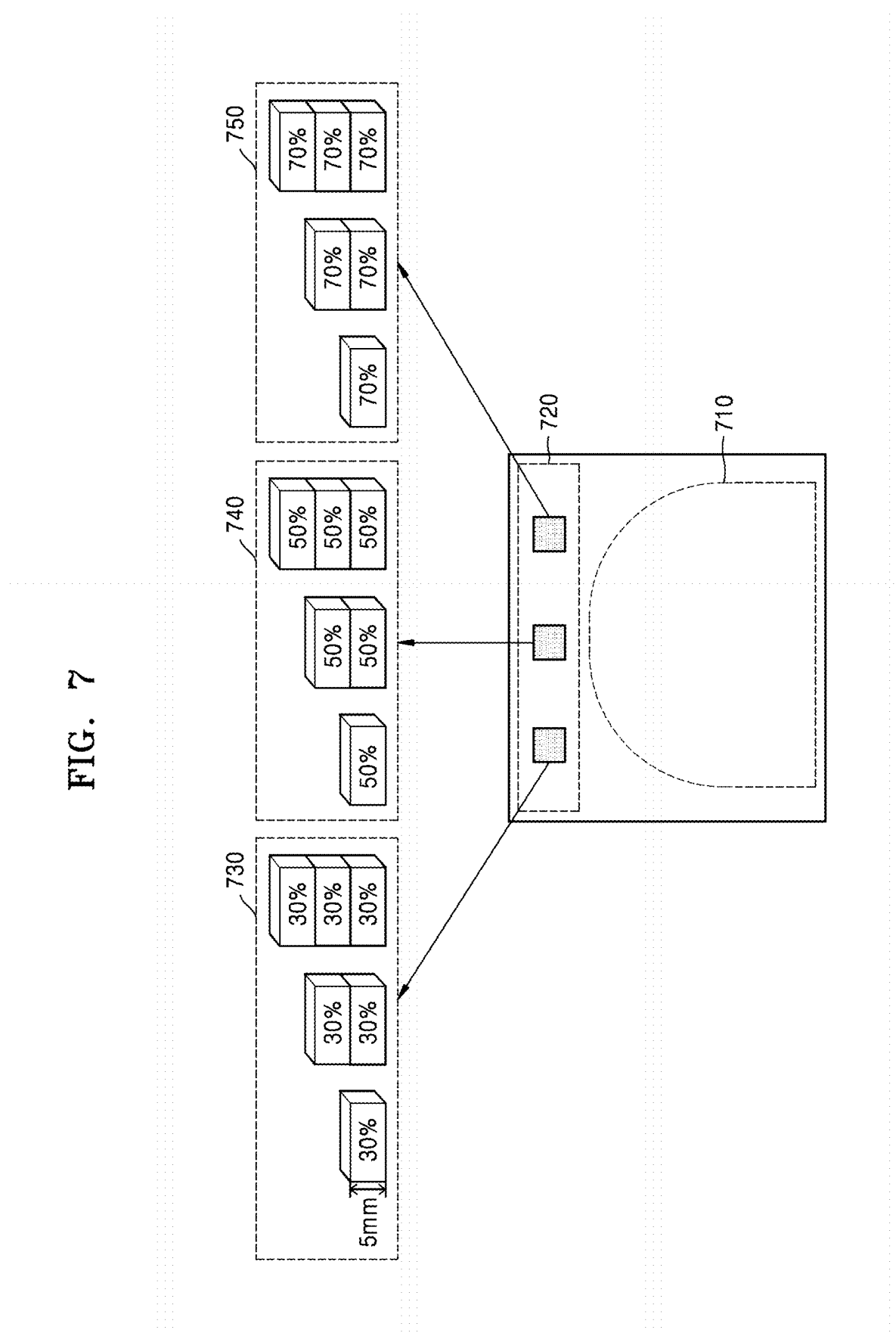
FIG. 7 is an exemplary diagram for describing calibration using a plurality of calibration phantoms according to an exemplary embodiment.

FIG. 7 is an exemplary diagram for describing calibration using a plurality of calibration phantoms according to an exemplary embodiment.

Referring to FIG. 7, the calibration phantoms 215 may include a plurality of calibration phantoms 730 which have a density of 30% and respectively have thicknesses of 5 mm, 10 mm, and 15 mm, a plurality of calibration phantoms 740 which have a density of 50% and respectively have thicknesses of 5 mm, 10 mm, and 15 mm, and a plurality of calibration phantoms 750 which have a density of 70% and respectively have thicknesses of 5 mm, 10 mm, and 15 mm.

For example, the detector 130 detects the X-rays having passed through the object on a region 710 and the calibration phantoms 215 may be disposed in order for the detector 130 to detect X-rays having passed through the calibration phantom 215 in a region 720 other than a region 710.

The medical imaging apparatus 200 according to an exemplary embodiment may acquire a pre-shot image from X-rays which are detected for each of the plurality of calibration phantoms 730, 740 and 750. The medical imaging apparatus 200 may acquire calibration information by using the acquired pre-shot image.

In detail, the medical imaging apparatus 200 may acquire, from the pre-shot image, a pixel value of the object and a pixel value for each of the plurality of calibration phantoms 730, 740 and 750. The medical imaging apparatus 200 may acquire a first relational equation between a thickness and a pixel value from the plurality of calibration phantoms 730, 740 and 750 having different thicknesses for each of a plurality of different densities by using the acquired pixel value. The medical imaging apparatus 200 may acquire a second relational equation between a density and a pixel value for a thickness of the object by using a plurality of the first relational equations acquired for the plurality of different densities. The medical imaging apparatus 200 may acquire a density of the object by using the second relational equation and a measured thickness and pixel value of the object. The medical imaging apparatus 200 may determine the second irradiating condition for main imaging by using the acquired density of the object.

The medical imaging apparatus 200 according to an exemplary embodiment may acquire, from the pre-shot image, the pixel value of the object and the pixel value for each of the plurality of calibration phantoms 730, 740 and 750. The medical imaging apparatus 200 may calculate a density of the object from the following Equation (1), which is the second relational equation for a thickness of the object, by using the acquired pixel value.

$$ob\_den = a \times ob\_PV + b \qquad \text{Equation (1)}$$

where ob_den denotes a density of the object,
ob_PV denotes a pixel value of the object, and
a and b denote coefficients which are calculated by using a pixel value and a density for each of the plurality of calibration phantoms 730, 740 and 750 having a certain thickness.

For example, a coefficient a may be calculated by the following Equation (2):

$$a = \frac{\sum_{i=1}^{N} x_i^2 \times \sum_{i=1}^{N} y_i - \sum_{i=1}^{N} x_i \times \sum_{i=1}^{N} x_i \times y_i}{N \times \sum_{i=1}^{N} x_i^2 - \sum_{i=1}^{N} x_i \times \sum_{i=1}^{N} x_i} \qquad \text{Equation (2)}$$

where N denotes the number of detected calibration phantoms,
$x_i$ denotes a pixel value for each of the detected calibration phantoms, and
$y_i$ denotes a density for each of the detected calibration phantoms.

For example, a coefficient b may be calculated by the following Equation (3):

$$b = \frac{\sum_{i=1}^{N} x_i^2 \times \sum_{i=1}^{N} y_i - \sum_{i=1}^{N} x_i \times \sum_{i=1}^{N} x_i \times y_i}{N \times \sum_{i=1}^{N} x_i^2 - \sum_{i=1}^{N} x_i \times \sum_{i=1}^{N} x_i} \qquad \text{Equation (3)}$$

where N denotes the number of detected calibration phantoms,
$x_i$ denotes a pixel value for each of the detected calibration phantoms, and
$y_i$ denotes a density for each of the detected calibration phantoms.

The medical imaging apparatus 200 may determine the second irradiating condition for main imaging by using the calculated density of the object.

Figure 8:
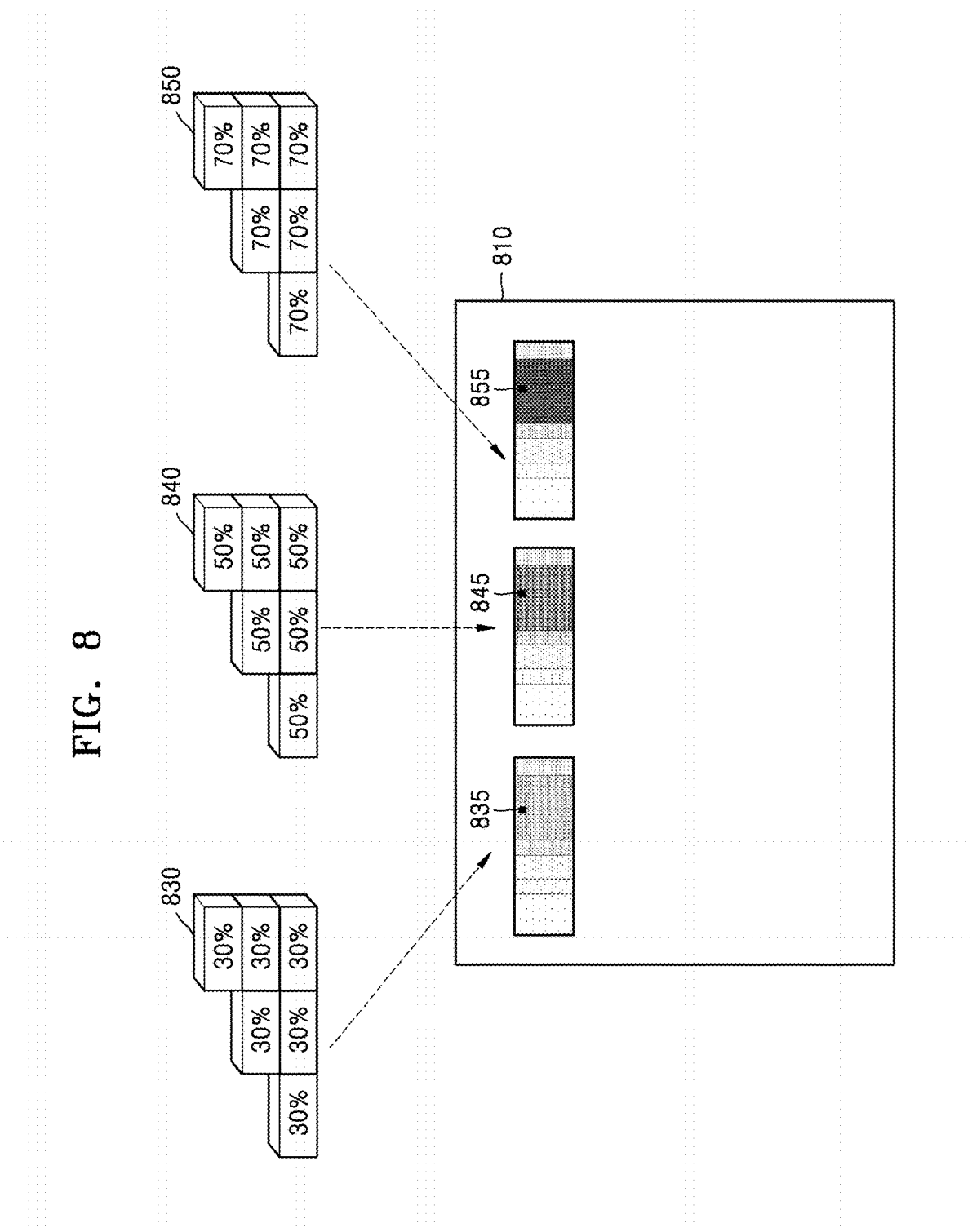
FIG. 8 is a diagram for describing a shape of a calibration phantom according to an exemplary embodiment.

FIG. 8 is a diagram for describing a shape of a calibration phantom according to an exemplary embodiment.

The calibration phantom 215 according to an exemplary embodiment may have a stairs shape to acquire data for different thicknesses.

Referring to FIG. 8, a calibration phantom 830 having a density of 30% may be provided in a three-step shape where a height of each step is 5 mm. In this case, calibration information in which thicknesses of the calibration phantom 830 having a density of 30% are 5 mm, 10 mm, and 15 mm may be acquired. Also, a calibration phantom 840 having a density of 50% may be provided in a three-step shape where a height of each step is 5 mm. In this case, calibration information in which thicknesses of the calibration phantom 840 having a density of 50% are 5 mm, 10 mm, and 15 mm may be acquired. Also, a calibration phantom 850 having a density of 70% may be provided in a three-step shape where a height of each step is 5 mm. In this case, calibration information in which thicknesses of the calibration phantom 850 having a density of 70% are 5 mm, 10 mm, and 15 mm may be acquired.

Referring to FIG. 8, a result 810 obtained by imaging the stairs-shaped calibration phantom 830 having a density of 30%, the stairs-shaped calibration phantom 840 having a density of 50%, and the stairs-shaped calibration phantom 850 having a density of 70% is shown. Referring to FIG. 8, a result 835 obtained by imaging the stairs-shaped calibration phantom 830 having a density of 30%, a result 845 obtained by imaging the stairs-shaped calibration phantom 840 having a density of 50%, and a result 855 obtained by imaging the stairs-shaped calibration phantom 850 having a density of 70% are shown. As seen in FIG. 8, as a thickness and/or a density of a calibration phantom increases, a pixel value becomes lower and, thus, a color of an image becomes darker.

Figure 9B:
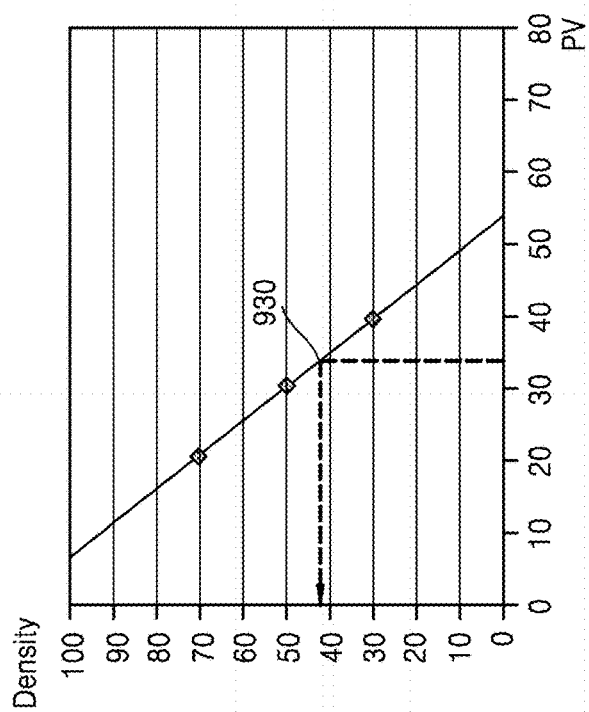
FIGS. 9A and 9B are diagrams for describing a method of acquiring calibration information by using calibration phantoms, according to an exemplary embodiment.
Figure 9A:
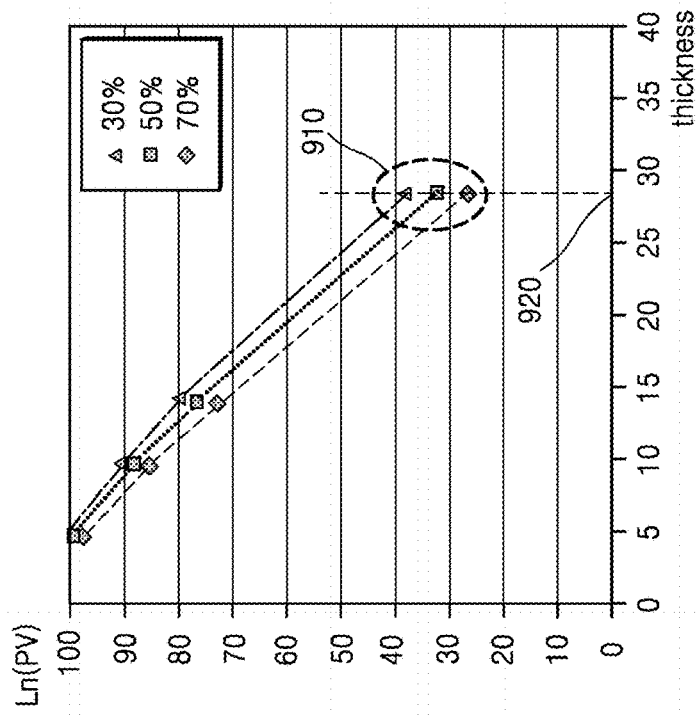

FIGS. 9A and 9B are diagrams for describing a method of acquiring calibration information by using a plurality of calibration phantoms, according to an exemplary embodiment.

FIG. 9A is a graph showing a relationship between pixel values based on thicknesses of calibration phantoms 215 having different densities. The medical imaging apparatus 200 may acquire density and pixel value information 910 corresponding to a measured thickness 920 of an object, for acquiring a relational equation between a pixel value and a density at a certain thickness.

FIG. 9B is a graph showing a relationship, acquired from the acquired density and pixel value information 910, between a density and a pixel value for a thickness 920 of the object. The medical imaging apparatus 200 may acquire a density 930 of an imaged object, corresponding to a pixel value of the object, from a relationship between a density and a pixel value for a thickness of the object. For example, when a pixel value PV of the object is 35, the density of the object may be calculated as 42%.

The medical imaging apparatus 200 may determine the second irradiating condition for main imaging by using an acquired density of an object. In this case, the medical imaging apparatus 200 may acquire a density of a region having the lowest pixel value among regions in which the object is imaged. This is for determining the second irradiating condition for main imaging in order for a high-density region to be well shown because a pixel value is lowered as a density becomes higher.

Figure 10A:
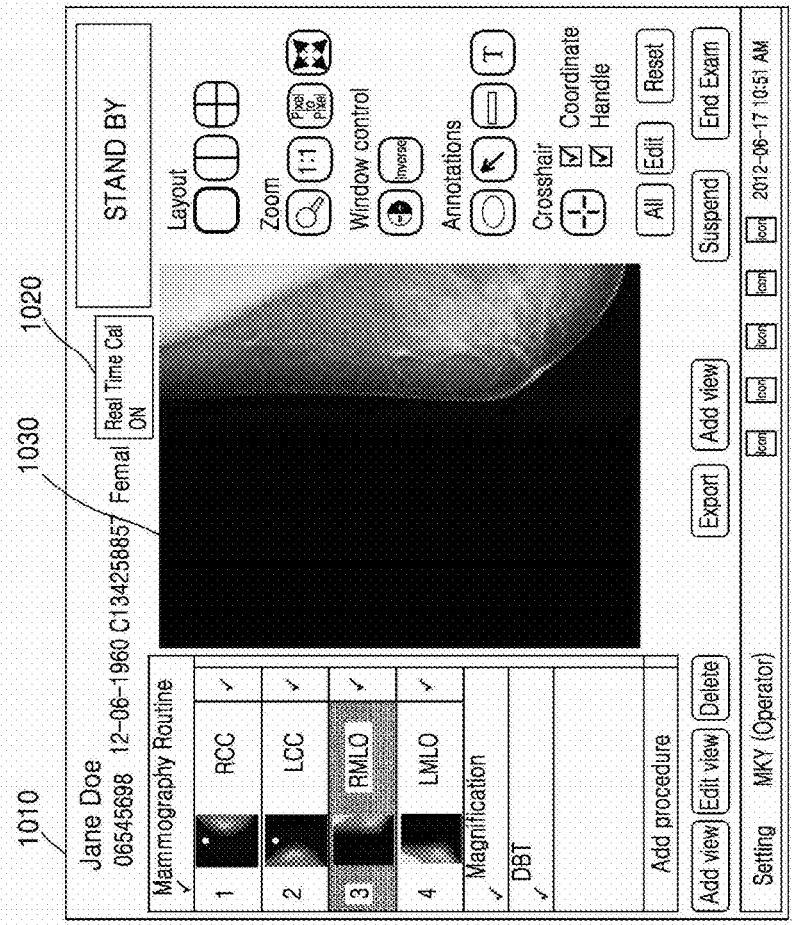
FIGS. 10A and 10B are exemplary diagrams illustrating a user interface for controlling the use of a calibration phantom, according to an exemplary embodiment.
Figure 10B:
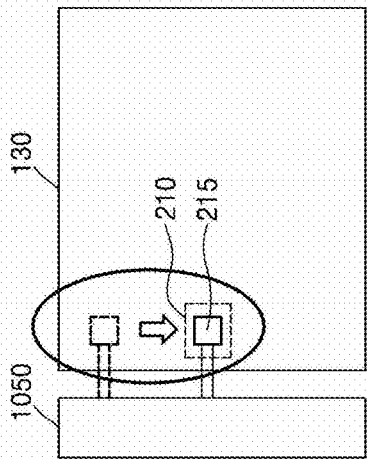

FIGS. 10A and 10B are exemplary diagrams illustrating a user interface (UI) 1010 for controlling the use of a calibration phantom 215 by a medical imaging apparatus 200 according to an exemplary embodiment.

A position 210 of the calibration phantom 215 according to an exemplary embodiment may be adjusted by controlling a support 1050 connected to the medical imaging apparatus 200. The support 1050 may be connected to, for example, the detector 130 or the X-ray radiation unit 120.

The medical imaging apparatus 200 according to an exemplary embodiment may display, on a screen 1030, an imaged object, whether to use the calibration phantom 215, and a position 210 of the calibration phantom 215 in the detector 130.

For example, referring to FIG. 10A, the UI 1010 may display information about the object, an imaging item, an imaged part, an input UI for controlling the detector 130, an indicator 1020 indicating whether the calibration phantom 215 is used, and an input UI for controlling a position 210 of the calibration phantom 215.

The medical imaging apparatus 200 according to an exemplary embodiment may control the support 1050 which supports the calibration phantom 215, thereby adjusting the position of the calibration phantom 215, for example, to a position 210.

For example, the medical imaging apparatus 200 may adjust the position of the calibration phantom 215, based on a user input.

For example, the output unit 350 of the medical imaging apparatus 200 may be a touch screen. The medical imaging apparatus 200 may receive a touch input for the position of the calibration phantom 215, through a region where an image acquired from the detector 130 is displayed on the touch screen. The medical imaging apparatus 200 may control the support 1050 in order for the calibration phantom 215 to be disposed in a region corresponding to a touch input of a user.

As another example, the medical imaging apparatus 200 may automatically adjust the position of the calibration phantom 215 so as not to overlap an object displayed on a screen. The medical imaging apparatus 200 may control the support 1050 in order for the calibration phantom 215 to be disposed in an arbitrary region of the detector 130 which does not overlap the object displayed on the screen.

Referring to FIG. 10B, the medical imaging apparatus 200 may adjust the position of the calibration phantom 215 by moving the support 1050 in a horizontal direction with respect to the detector 130.

Figure 11B:
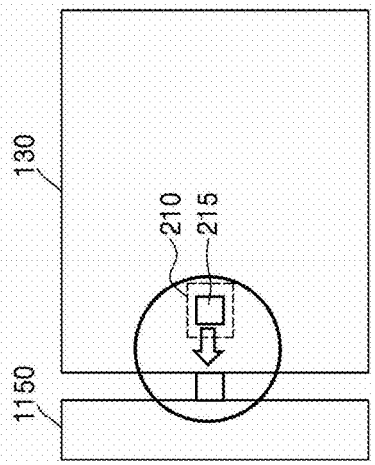
FIGS. 11A and 11B are exemplary diagrams illustrating a user interface for controlling the use of a calibration phantom, according to an exemplary embodiment.
Figure 11A:
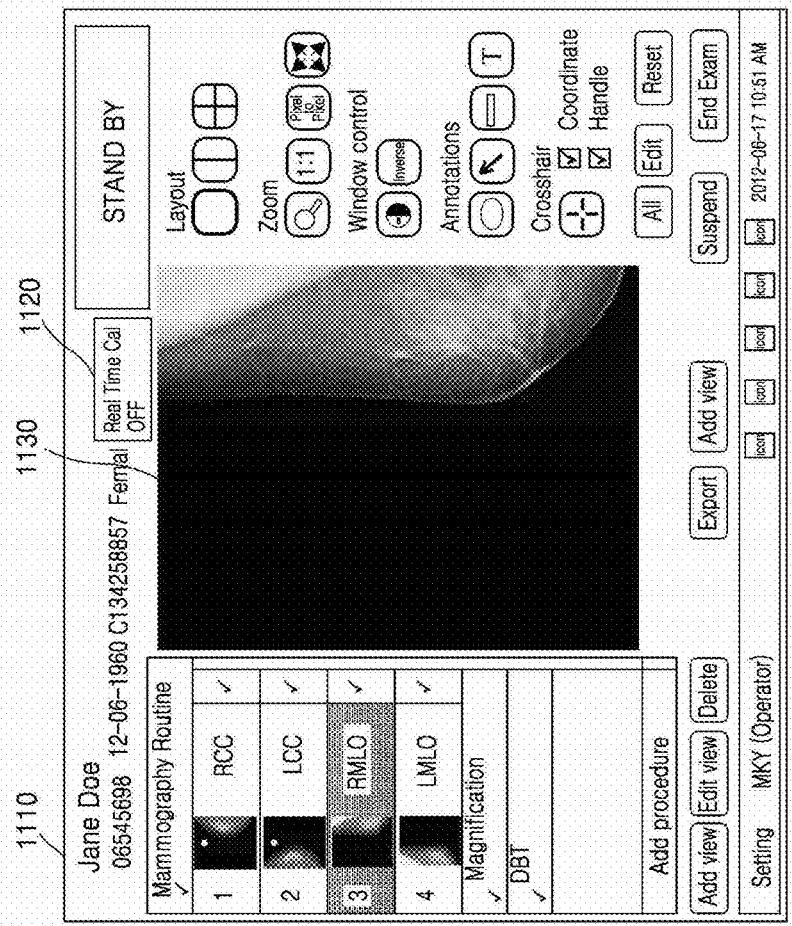

FIGS. 11A and 11B are exemplary diagrams illustrating a user interface (UI) 1110 for controlling the use of a calibration phantom 215 by a medical imaging apparatus 200 according to an exemplary embodiment.

The medical imaging apparatus 200 according to an exemplary embodiment may display, on a screen 1130, an imaged object, whether to use the calibration phantom 215, and a position 210 of the calibration phantom 215 on the detector 130.

For example, referring to FIG. 11A, the UI 1110 may display information about the object, an imaging item, an imaged part, an input UI for controlling the detector 130, an indicator 1120 indicating whether to use the calibration phantom 215, and an input UI for controlling a position 210 of the calibration phantom 215.

The medical imaging apparatus 200 according to an exemplary embodiment may control a support 1150 which supports the calibration phantom 215, thereby controlling whether to use the calibration phantom 215. For example, the medical imaging apparatus 200 may determine whether to use the calibration phantom 215, based on a user input.

Referring to FIG. 11B, when the calibration phantom 215 is determined not to be used, the medical imaging apparatus 200 may control the support 1150 in order for the calibration phantom 215 to be disposed outside the detector 130. For example, the medical imaging apparatus 200 may perform control to reduce a distance between a connection portion of the support 1150 and the calibration phantom 215, and, thus, the calibration phantom 215 may be disposed outside the detector 130.

FIG. 12 is a flowchart illustrating a control method of a medical imaging apparatus 200 according to an exemplary embodiment.

Detailed operation of the medical imaging apparatus 200 according to an exemplary embodiment is described above with reference to FIGS. 1 to 11. Therefore, in describing the control method of the medical imaging apparatus 200, the same descriptions provided with regard to FIGS. 1 to 11 are not repeated.

In operation 1210, the medical imaging apparatus 200 irradiates X-rays onto an object and the calibration phantom 215, which is disposed not to overlap the object, according to the first irradiating condition for pre-shot.

In operation 1220, the medical imaging apparatus 200 detects the X-rays having passed through the object and the calibration phantom 215.

In operation 1230, the medical imaging apparatus 200 acquires calibration information by using a pre-shot image acquired from the detected X-rays.

The medical imaging apparatus 200 may acquire a density of the object, based on a pixel value of the calibration phantom 215 included in the pre-shot image.

The calibration phantom 215 according to an exemplary embodiment may have a single thickness and a single density. The medical imaging apparatus 200 may perform offset correction on pre-stored calibration information by using the pre-shot image acquired from the detected X-rays having passed through the calibration phantom 215.

The calibration phantom 215 according to another exemplary embodiment may include a plurality of calibration phantoms 215 in which at least one calibration phantom has a thickness and/or a density different from other calibration phantoms. The medical imaging apparatus 200 may acquire a pre-shot image from X-rays detected for a plurality of the calibration phantoms 215 and acquire calibration information by using the acquired pre-shot image.

For example, the medical imaging apparatus 200 may acquire, from the pre-shot image, a pixel value of the object and a pixel value for each of the plurality of calibration phantoms 215. The medical imaging apparatus 200 may acquire a first relational equation between a thickness and a pixel value from the plurality of calibration phantoms 215 having different thicknesses for each of a plurality of different densities by using the acquired pixel value. The medical imaging apparatus 200 may acquire a second relational equation between a density and a pixel value for a thickness of the object by using a plurality of the first relational equations acquired for the plurality of different densities. The medical imaging apparatus 200 may acquire a density of the object by using the second relational equation and a pixel value of the imaged object.

In operation 1240, the medical imaging apparatus 200 determines the second irradiating condition for main imaging by using the acquired calibration information. The medical imaging apparatus 200 may determine the second irradiating condition, based on the acquired density of the object.

The medical imaging apparatus 200 according to an exemplary embodiment may display an image of an object which is imaged according to the second irradiating condition.

The medical imaging apparatus 200 may display a usage state of the calibration phantom 215. The usage state may include at least one selected from whether to use the calibration phantom 215, a position of the calibration phantom 215 in the detector 130, and whether the calibration phantom 215 is currently used.

Therefore, according to an exemplary embodiment, because there is no difference between a timing when calibration is performed and a timing when an object is actually imaged, an accuracy of calibration is prevented from being reduced when pieces of system information differ. That is, according to an exemplary embodiment, calibration information is acquired in real time while imaging an object, and calibration is performed, thereby enhancing a performance of the medical imaging apparatus 200.

For example, based on experiments conducted for an imaged object having a density of 30%, it was determined by a related art method that a density of the object is 30%, but according to an exemplary embodiment, a result in which a density of the object is determined as 31% was acquired. According to an exemplary embodiment, it is proved that an accuracy of a diagnosis increases.

The above-described exemplary embodiments may be written as computer programs and may be implemented in digital computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs, etc.), and transmission media such as Internet transmission media.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A medical imaging apparatus comprising:
a calibration phantom;
an X-ray radiation unit configured to radiate X-rays onto an object and onto the calibration phantom, which does not overlap the object, according to a first irradiating condition for a pre-shot;
a detector configured to detect the X-rays having passed through the object and through the calibration phantom; and
a controller configured to acquire calibration information by using a pre-shot image acquired from the detected X-rays, and determine a second irradiating condition for main imaging by using the calibration information.

2. The medical imaging apparatus of claim 1, wherein the controller is configured to acquire a density of the object, based on a pixel value of the calibration phantom included in the pre-shot image.

3. The medical imaging apparatus of claim 2, wherein the controller is configured to determine the second irradiating condition, based on the density of the object acquired based on the pre-shot image.

4. The medical imaging apparatus of claim 1, wherein the calibration phantom comprises a first calibration phantom having a single thickness and a single density, and
the controller is configured to perform offset correction on pre-stored calibration information by using the pre-shot image acquired from the detected X-rays having passed through the first calibration phantom.

5. The medical imaging apparatus of claim 4, further comprising second calibration phantoms,
wherein the controller is further configured to acquire an image of the second calibration phantoms before the pre-shot image, and to acquire the pre-stored calibration information from the image of the second calibration phantoms.

6. The medical imaging apparatus of claim 1, wherein the calibration phantom comprises third calibration phantoms,
at least one of the third calibration phantoms has at least one of a thickness and a density different from other ones of the third calibration phantoms, and
the controller is configured to acquire the pre-shot image from the X-rays detected for the third calibration phantoms, and acquire the calibration information by using the acquired pre-shot image.

7. The medical imaging apparatus of claim 6, wherein the third calibration phantoms have at least one of the thickness and the density different from one another, and
the controller is configured to acquire, from the pre-shot image, a pixel value of the object and a pixel value for each of the third calibration phantoms, acquire respective first relational equations between the thickness and the pixel value of the third calibration phantoms having thicknesses different from one another, for each of different densities by using the acquired pixel value, acquire a second relational equation between the density and the pixel value for a thickness of the object by using the respective first relational equations, acquire a density of the object by using the second relational equation and the pixel value of the object, and determine the second irradiating condition for the main imaging by using the acquired density of the object.

8. The medical imaging apparatus of claim 6, wherein the third calibration phantoms have at least one of the thickness and the density different from one another, and
the controller is configured to acquire a pixel value of the object and a pixel value for each of the third calibration phantoms from the pre-shot image, calculate a density of the object by using the acquired pixel value, and determine the second irradiating condition for the main imaging by using the calculated density of the object, wherein the density of the object is calculated as:

$$ob\_den = a \times ob\_PV + b$$

where ob_den is the density of the object,
ob_PV is the pixel value of the object, and
a and b are coefficients which are calculated by using the pixel value and the density for each of the third calibration phantoms.

9. The medical imaging apparatus of claim 1, wherein the calibration phantom is disposed on the detector.

10. The medical imaging apparatus of claim 1, wherein the calibration phantom is disposed between the X-ray radiation unit and the detector.

11. The medical imaging apparatus of claim 1, wherein the calibration phantom has a stairs shape having thicknesses which vary stepwise, to acquire data for different thicknesses of the calibration phantom.

12. The medical imaging apparatus of claim 1, further comprising:
a display device configured to display an image of the object which is imaged according to the second irradiating condition.

13. The medical imaging apparatus of claim 12, wherein the display device is configured to display a usage state of the calibration phantom, and
the usage state comprises at least one of whether the calibration phantom is being used and a position of the calibration phantom in the detector.

14. The medical imaging apparatus of claim 1, further comprising a support which supports the calibration phantom,
wherein the controller is configured to control the support to adjust a position of the calibration phantom.

15. A control method for a medical imaging apparatus, the control method comprising:
radiating X-rays onto an object and onto a calibration phantom, which does not overlap the object, according to a first irradiating condition for a pre-shot;
detecting the X-rays having passed through the object and through the calibration phantom;
acquiring calibration information by using a pre-shot image acquired from the detected X-rays; and
determining a second irradiating condition for main imaging by using the calibration information.

16. The control method of claim 15, wherein the acquiring the calibration information comprises acquiring a density of the object, based on a pixel value of the calibration phantom included in the pre-shot image, and
the determining the second irradiating condition comprises determining the second irradiating condition, based on the density of the object.

17. The control method of claim 15, wherein the calibration phantom comprises a first calibration phantom having a single thickness and a single density, and
the acquiring the calibration information comprises performing offset correction on pre-stored calibration information by using the pre-shot image acquired from the detected X-ray having passed through the first calibration phantom.

18. The control method of claim 15, further comprising: disposing the calibration phantom not to overlap the object on a detector.

19. The control method of claim 15, further comprising: displaying an image of the object which is imaged according to the second irradiating condition.

20. A medical imaging apparatus comprising:
an X-ray irradiation unit configured to generate an X-ray to irradiate a first amount of the X-ray onto an object;
an image acquisition unit comprising one or more calibration phantoms, configured to receive the X-ray irradiated onto the object, acquire X-ray image information of the object, and acquire calibration phantom image information and the X-ray image information of the object when the X-ray is irradiated onto the object and onto the one or more calibration phantoms; and
at least one processor configured to correct an irradiating condition based on the calibration phantom image information,
wherein the at least one processor is further configured to control the X-ray irradiation unit to irradiate a second amount of the X-ray corresponding to a density of the object based on the corrected irradiation condition.

21. The medical imaging apparatus of claim 20, wherein the image acquisition unit comprises a detector or a bucky, and
the one or more calibration phantoms are coupled to one selected from the detector and the bucky.

22. A method of controlling a medical imaging apparatus, the method comprising:
irradiating a first amount of X-rays onto an object;
acquiring X-ray image information of the object and X-ray image information of a calibration phantom;
correcting an irradiating condition based on the X-ray image information of the calibration phantom; and
irradiating a second amount of X-rays corresponding to a density of the object, based on a result of the correcting.

23. The method of claim 22, wherein the correcting the irradiating condition comprises correcting an X-ray irradiation amount based on a density of the calibration phantom.

24. The method of claim 22, wherein the irradiating the first amount of X-rays comprises determining the density of the object.

* * * * *